United States Patent [19]

Müller et al.

[11] Patent Number: 5,467,494
[45] Date of Patent: Nov. 21, 1995

[54] TOOTHBRUSH

[75] Inventors: Ingo Müller, Klagenfurt; Norbert Schneider, Ebental, both of Austria

[73] Assignee: U.S. Philips Corporation, New York, N.Y.

[21] Appl. No.: 280,914

[22] Filed: Jul. 27, 1994

[30] Foreign Application Priority Data

Jul. 30, 1993 [BE] Belgium ............... 09300812

[51] Int. Cl.[6] .................. A61C 17/34; A46B 13/02
[52] U.S. Cl. ...................... 15/22.1; 15/167.1
[58] Field of Search ................ 15/22.1, 22.2, 15/224, 167.1, 167.2, 172

[56] References Cited

U.S. PATENT DOCUMENTS 3,493,991  2/1970  De Bianchi ............... 15/143.1

FOREIGN PATENT DOCUMENTS 0481553  4/1992  European Pat. Off. ........ 15/22.1
2550068  2/1985  France ..................... 15/167.1
2002159  2/1992  WIPO ...................... 15/22.1
2010979  7/1992  WIPO ...................... 15/22.1

Primary Examiner—Edward L. Roberts, Jr.
Attorney, Agent, or Firm—Ernestine C. Bartlett

[57] ABSTRACT

A toothbrush comprises two parts (2, 3) which are pivotable relative to one another, of which a first part (2) serves as a handle and of which a second part (3) carries a brush-head (5), a spring (7) being arranged between the parts and having one end (8) fixedly connected to one (2) of the parts and having another end (9) which engages with a wall portion (11) of the second part (3), the second part (3) being pivotable relative to the first part (2) against a pressure exerted by the spring (7) during use of the toothbrush, which spring snaps when a given pressure threshold ($P_d$) is exceeded, after which the second part (3) is subjected only to a bending load in the absence of a pressure (Q) directed in the longitudinal direction of the spring (7) and exerted by the wall portion (11), and resumes its original position when the pressure has decreased.

5 Claims, 3 Drawing Sheets

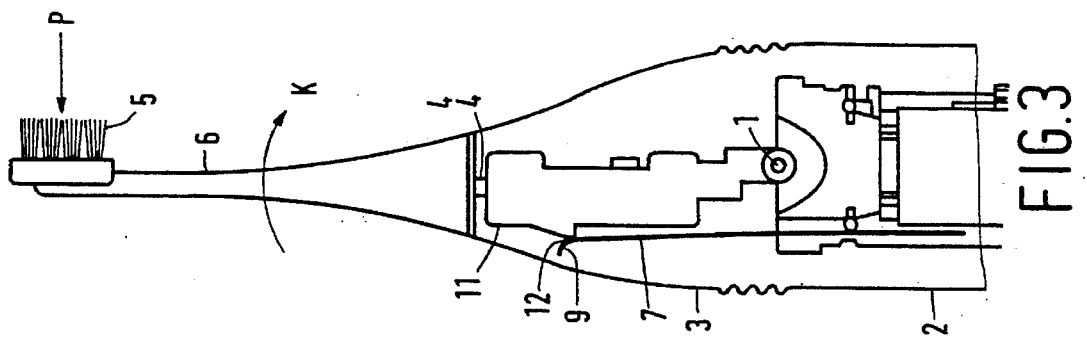
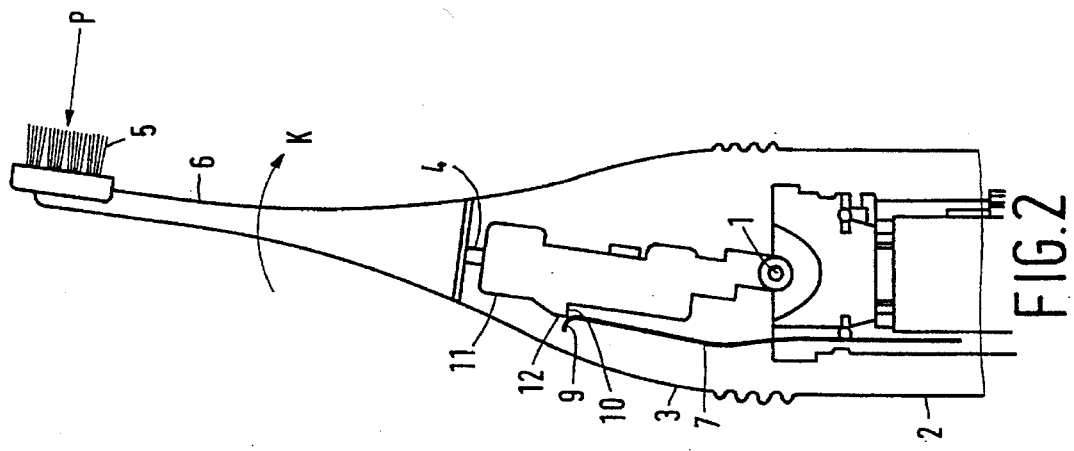
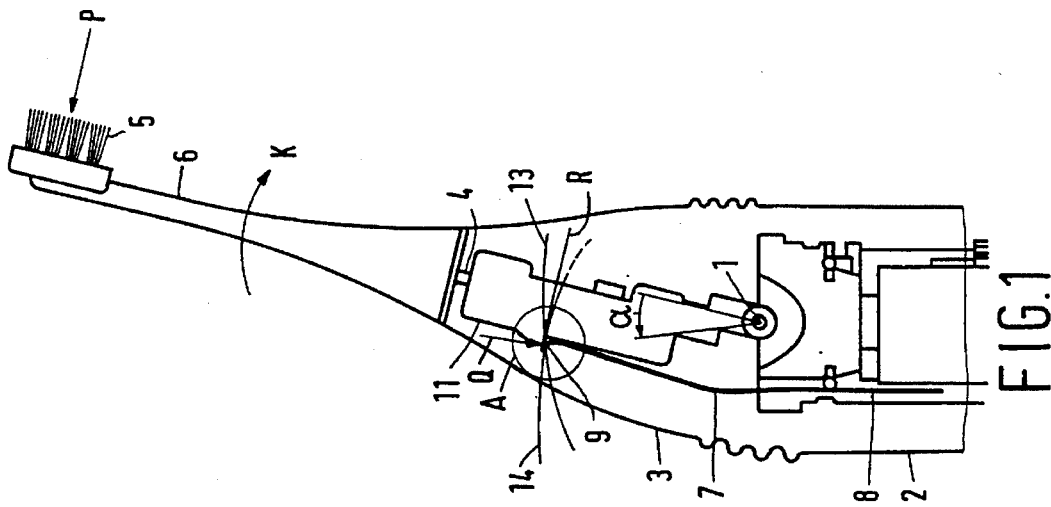

TOOTHBRUSH

FIELD OF THE INVENTION

The invention relates to a toothbrush comprising two parts which are pivotable relative to one another, of which a first part serves as a handle and of which a second part carries a brush-head, a spring being arranged between the parts and having one end fixedly connected to one of the parts, the second part being pivotable relative to the first part against a pressure exerted by the spring during use of the toothbrush, which spring snaps when a given pressure threshold is exceeded and resumes its original position when the pressure has decreased.

BACKGROUND OF THE INVENTION

Snapping is to be understood to mean a suddenly occurring acceleration or deceleration.

Such a toothbrush is known from DE-A-37 24 476.

The force with which the brush is pushed against the teeth is important for a proper cleaning action. To remove dental plaque a certain pressure must be applied. However, the brushing pressure should not be too high because the brush also comes into contact with the gums and the tooth necks during brushing. DE-A-37 24 476 describes a tooth brush which provides protection against an excessive brushing pressure. For this purpose a blade spring is fitted with its two ends in facing slots in the parts. A drawback of this construction is that after a pressure threshold at which the snap action of the spring occurs has been exceeded the reset force of the spring (and, as a consequence, the brushing pressure) becomes indeterminate.

SUMMARY OF THE INVENTION

An object of the invention is to provide a toothbrush which has a well-defined, reproducible and adequate reset force after the spring has snapped.

To this end the invention is characterized in that in a toothbrush comprising two parts which are pivotable relative to each other, one of such parts has a wall portion, which wall portion, in a situation after snapping of the spring, follows a path which differs from the path of the spring end portion which engages against the wall portion before snapping, the spring being subjected only to a bending load in the absence of a pressure directed in the longitudinal direction of said spring and exerted by the wall portion.

When a given pressure threshold is reached the end of the spring suddenly disengages from the wall portion, which after this is only subjected to a bending load of the spring.

An advantage of the toothbrush in accordance with the invention is that the user of such a toothbrush may readily proceed with brushing after a given pressure threshold (for example 2 to 3N) has been exceeded, because after snapping of the spring the part with the brush-head is only subjected to a bending load which results in a pressure which is sufficiently high and well-defined but smaller than the threshold value, so that the brushing pressure does not become too high. After the brushing pressure exerted on the teeth has decreased or ceased, the part with the brush-head returns to its initial position. It is obvious that the pivotal movement of the parts is limited by means of a stop. This stop is arranged in such a way that brushing in this position hardly ever occurs in practice but is possible.

A preferred embodiment of the toothbrush is characterized in that the wall portion of the relevant part has two surfaces forming an angle with one another, the end portion of the spring being in contact with a first surface before snapping and being in contact with the other second surface after snapping. This results in a simple construction for the snap action of the spring.

Preferably, the toothbrush is characterized in that the spring has a linear characteristic after snapping.

BRIEF DESCRIPTION OF THE DRAWINGS

An embodiment of the invention will now be described in more detail, by way of example, with reference to the drawings. In the drawings:

FIG. 1 shows a toothbrush before snapping,

FIG. 2 shows the toothbrush of FIG. 1 in a situation at the instant of snapping, FIG. 3 shows the toothbrush of FIG. 1 in a situation after snapping.

DETAILED DESCRIPTION OF THE PREFERRED EMBODIMENTS

Figure 4:
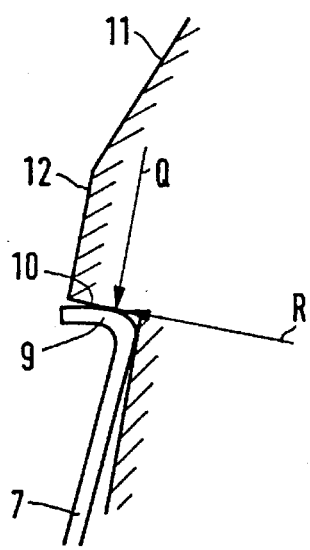
FIG. 4 shows a part of the toothbrush as indicated by the circle A.

The toothbrush in accordance with the invention has two parts 2 and 3 which are connected to one another by a pivot 1. The first part 2 serves as a handle. The second part has a drive shaft 4. A brush shank 6 carrying a brush-head 5 can be detachably coupled to the drive shaft 4. A spring 7 is arranged between the parts 2 and 3. One end 8 of the spring is fixedly connected to the part 2. At its other end 9 the spring 7 is slightly bent and this bent end portion 9 engages against a first contact surface 10 of a wall portion 11 of the part 3. This wall portion has a second contact surface 12 directly adjoining the surface 10.

FIG. 1 shows the toothbrush in its initial position, i.e. in a position in which no brushing takes place and no force is exerted on the brush-head 5. The spring 7 has a certain pretension, which urges the part 3 with the brush-head in a clockwise direction K. The bent end portion 9 of the spring engages against the first contact surface 10 of the wall portion 11 (see also FIG. 4). During brushing the brush-head 5 is subjected to a force P which opposes the pretension of the spring. If the force P becomes larger than the pretension the part 3 will be pivoted relative to the part 2 in a direction opposite to the direction K, i.e. anti-clockwise. The contact surface 10 exerts a pressure Q in the longitudinal direction of the spring, which pressure increases as the force P increases and which tends to cause the end portion 9 of the spring to snap off its contact surface 10. The bent end portion 9 of the spring 7 and the first contact surface 10 follow the same path 13 until snapping occurs.

FIG. 2 shows the toothbrush in a position in which the force P has become so large that the spring has reached its snapping position. The force R, which is directed transversely of the force Q and which is caused by the bending moment at the end of the spring, has then become so large that the bent end portion 9 of the spring is urged away from its contact surface 10. The end portion 9 then in fact springs away from the contact surface 10. After snapping the path 14 of the end portion 9 of the spring 7 is different from the path 13 of the wall portion 10.

As is shown in FIG. 3, the portion adjoining the bent end portion of the spring then directly engages against a second contact surface 12 of the part 3. The pressure in the longitudinal direction of the spring is then absent. The part 3 with the brush-head 5 is now only subjected to a bending load, which tends to urge the part 3 back into its original position. In this situation brushing may readily be continued until an instant at which, for example, the brush is moved to another spot to be cleaned. The pressure of the brush-head on the teeth then decreases or ceases and the part with the brush-head resumes its original position under the influence of the bending force of the spring.

Figure 5:
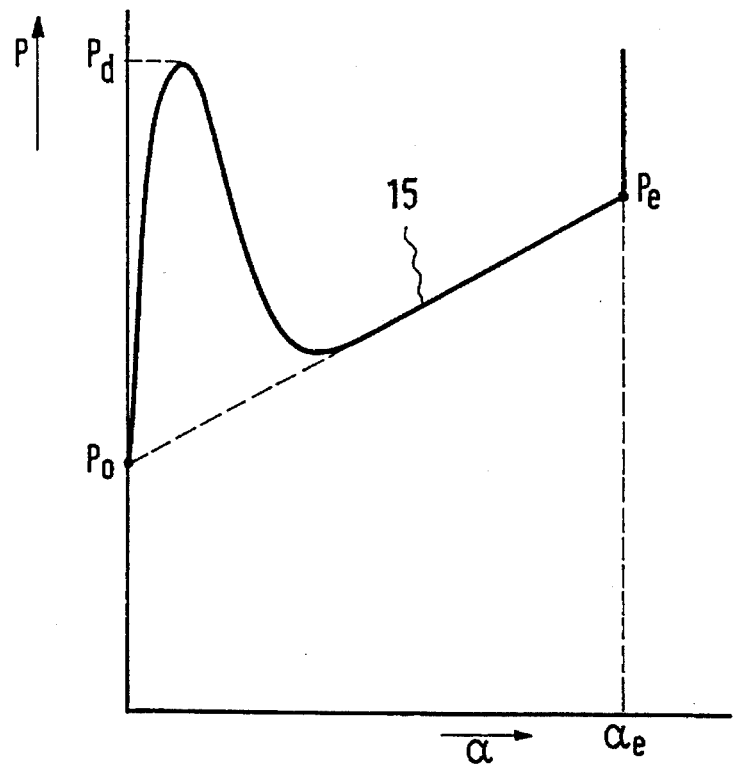
FIG. 5 is a graph showing the force exerted on the brush-head as a function of the angular rotation of the brush-head.

FIG. 5 shows the force P on the brush-head as a function of the angular rotation $\alpha$ of the part 3 relative to the part 2. The angular rotation $\alpha$ is only small until a given threshold value $P_d$ of the pressure P is reached, which value is 2 to 3N. After snapping of the spring with an angular rotation $\alpha_d$ the brush-head is only subjected to a bending stress, as is indicated by a straight line 15. After an angular rotation $\alpha_e$ the brush-head is prevented from rotating any further by a stop (not shown) between the parts 2 and 3. The pressure $P_e$ corresponding to this angular rotation is smaller than the threshold value $P_d$. If the pressure on the brush-head ceases the brush-head will resume its initial position $\alpha_o$. The initial force $P_o$ on the brush-head is caused by the pretension in the spring.

Figure 6:
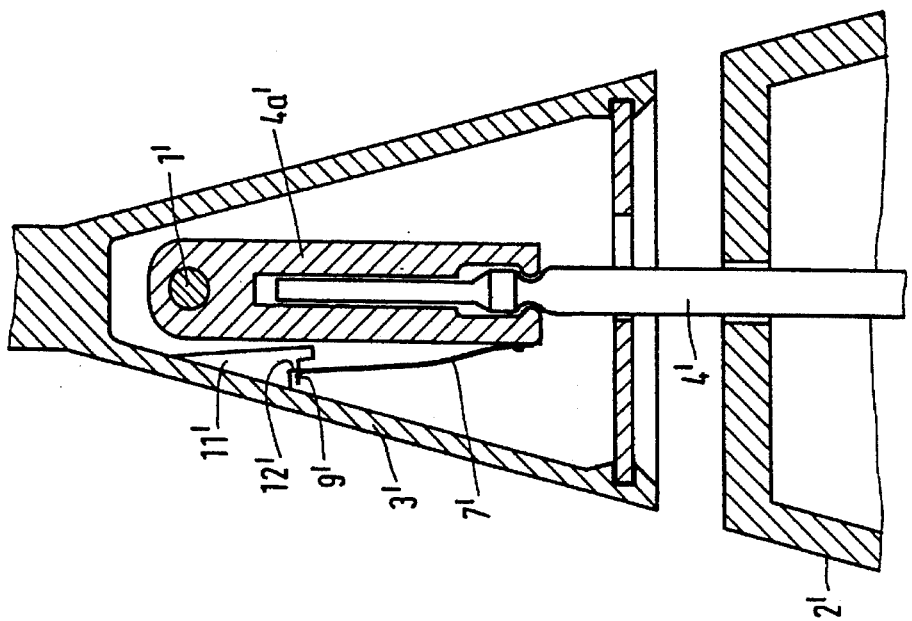
FIGS. 6 and 7 shows a toothbrush in a second embodiment.
Figure 7:
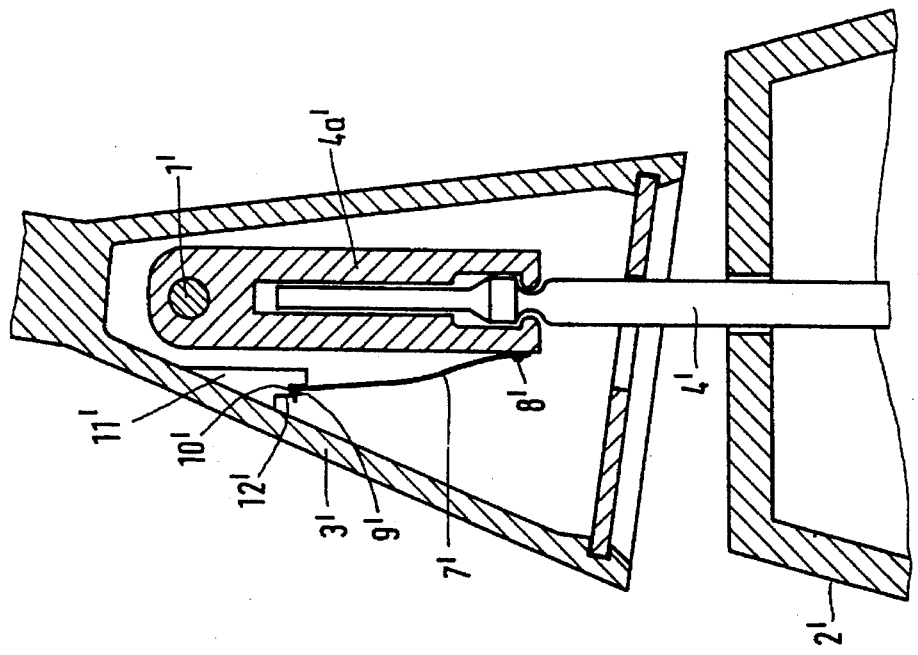

FIGS. 6 and 7 show another embodiment of the toothbrush in accordance with the invention. In this embodiment a drive shaft 4' is pivotably connected to the second part 3'. For this purpose the second part 3' is provided with a coupling member 4a', which is pivotable about a pivot 1' and can be coupled to the drive shaft 4'. A brush-head, not shown, and the second part 3' may be integral with one another, or the brush-head may be detachably connected to the second part 3'. A spring 7' has one end 8' fixedly connected to the coupling member 4a'. At its other end it has a bent end portion 9', which engages against a first contact surface 10' of a wall portion 11' of the second part 3'. Since the drive shaft 4' belongs to the first part 2' and the coupling member 4a' is fixedly connected to the drive shaft the spring 7' in the present embodiment may also be said to be disposed between the parts 2' and 3'. In the same way as in the embodiment described with reference to FIGS. 1–3, the spring will snap when a given pressure threshold has been exceeded, i.e. the end 9' of the spring snaps off the first contact surface 10' and engages against the second contact surface 12', after which the second part 3' is subjected only to a bending stress. The manner in which the spring 7' snaps and springs back is based on the same principle, i.e. the path of the wall portion 10' and the path of the end portion 9' of the spring are the same before snapping of the spring and differ after snapping.

The toothbrush shown in the Figures is an electric toothbrush, in which the drive shaft is driven by a motor. However, the toothbrush may also be a normal hand-operated toothbrush.

We claim:

1. A toothbrush comprising two parts (2,3) which are pivotable relative to one another, of which a first part (2) serves as a handle and of which a second part (3) carries a brush-head (5), a spring (7) being arranged between the parts, said spring having one end portion (9) in contact with a portion of one of the parts (3) and having one end portion (8) fixedly connected to one of the parts (2), the second part (3) being pivotable relative to the first part (2) against a pressure exerted by the spring (7) during use of the toothbrush, which spring snaps from a point of contact with the part (3) when a given pressure threshold ($P_d$) is exceeded and resumes said point of contact with the part (3) when the pressure has decreased, wherein the part (3) has a wall portion (11), which wall portion (11), in a situation after snapping of the spring (7), follows a path (13) which differs from the path (14) of the spring end portion (9) which engages against said wall portion (11) before snapping of the spring (7), the spring being subjected only to a bending load in the absence of a pressure (Q) directed in the longitudinal direction of said spring and exerted by the wall portion (11).

2. A toothbrush as claimed in claim 1, wherein the wall portion (11) of the relevant part (3) has two surfaces (10, 12) forming an angle with one another, the end portion (9) of the spring being in contact with a first surface (10) before snapping and being in contact with the other second surface (12) after snapping.

3. A toothbrush as claimed in claim 1 wherein the spring has an elongated shape and has a linear characteristic after snapping.

4. A toothbrush as claimed in claim 2 wherein the spring has an elongated shape and has a linear characteristic after snapping.

5. A toothbrush which comprises two parts which are pivotable relative to one another, of which a first part serves as a handle and a second part carries a brush head, a spring being arranged between the parts and having one end fixedly connected to the first part and having the other end in contact with a wall portion of the second part, the second part being pivotable relative to the first part against a given pressure threshold ($P_d$) exerted by the spring during use of the toothbrush, wherein said spring:

(1) snaps out of contact with said wall when said pressure threshold ($P_d$) is exceeded, after which the second part is subjected only to a bending load in the absence of a pressure (Q) directed in the longitudinal direction of the spring and exerted by said wall portion, and (2) resumes its original position whereby one end contacts said wall portion when said exceeded pressure threshold ($P_d$) has decreased.

* * * * *